(12) United States Patent
Mikhailov et al.

(10) Patent No.: US 8,873,701 B2
(45) Date of Patent: *Oct. 28, 2014

(54) METHOD FOR DETERMINING SPATIAL DISTRIBUTION AND CONCENTRATION OF A COMPONENT IN A PORE VOLUME OF A POROUS MATERIAL

(75) Inventors: Dmitry Mikhailov, Moscow (RU); Alexander Nadeev, Moscow (RU); Vadim Khlebnikov, Moscow (RU); Pavel Zobov, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 231 days.

This patent is subject to a terminal disclaimer.

(21) Appl. No.: 13/531,338

(22) Filed: Jun. 22, 2012

(65) Prior Publication Data

US 2013/0010918 A1    Jan. 10, 2013

(30) Foreign Application Priority Data

Jun. 23, 2011   (RU) .................................. 2011125733

(51) Int. Cl.
*A61B 6/03* (2006.01)
*G01N 23/04* (2006.01)
*G01N 33/24* (2006.01)

(52) U.S. Cl.
CPC ................ *G01N 23/04* (2013.01); *G01N 33/24* (2013.01); *G01N 2223/404* (2013.01); *G01N 2223/649* (2013.01)
USPC .................................... 378/4; 378/53; 378/54

(58) Field of Classification Search
CPC ..... G01N 33/24; G01N 23/04; G01N 23/046; G01N 2223/404; G01N 2223/419; G01N 2223/649

USPC ....................................... 378/4, 53, 54, 55, 56
See application file for complete search history.

(56) References Cited

U.S. PATENT DOCUMENTS

| 4,540,882 A | 9/1985 | Vinegar et al. |
| 4,649,483 A | 3/1987 | Dixon |
| 4,688,238 A | 8/1987 | Sprunt et al. |

(Continued)

FOREIGN PATENT DOCUMENTS

| RU | 2207808 C1 | 7/2003 |
| RU | 2360233 C1 | 6/2009 |
| SU | 1122951 A1 | 11/1984 |
| SU | 1679294 A1 | 9/1991 |

OTHER PUBLICATIONS

Gonzalez, et al., "Digital Image Processing", Prentice-Hall, Inc.: Upper Saddle River, NJ, 2nd Edition, 2002, 15 pages.

*Primary Examiner* — Glen Kao

(57) ABSTRACT

A water-soluble salt of a metal with a high atomic weight is selected as an X-ray contrast substance providing a selective ion-exchange reaction with a component. The salt has a general formula $R^+M^-$, where $R^+$ is selected from a group consisting of $Ba^{2+}$; $Sr^{2+}$; $Tl^+$; $Rb^+$ . . . , and $M^-$ is selected from a group consisting of $Cl_n$; $NO_n$; $OHn$; $CH3COO$, $SO_4$; . . . in accordance with a standard table of inorganic substances' water solubility. The X-ray contrast substance is injected into a sample of a porous material. Upon completion of the selective ion exchange reaction a non-contrast displacing agent is injected into the sample. The sample is scanned by computer X-ray microtomography and spatial distribution and concentration of the component in question is estimated by analysis of the obtained computer tomographic image of the sample.

2 Claims, 2 Drawing Sheets

(56) References Cited

U.S. PATENT DOCUMENTS

| | | |
|---|---|---|
| 4,722,095 A | 1/1988 | Muegge et al. |
| 4,799,382 A | 1/1989 | Sprunt et al. |
| 4,982,086 A | 1/1991 | Withjack |
| 5,027,379 A | 6/1991 | Hunt et al. |
| 5,469,488 A | 11/1995 | Ono |
| 2005/0010106 A1 | 1/2005 | Lang et al. |
| 2005/0136002 A1 | 6/2005 | Fossheim et al. |
| 2013/0010919 A1* | 1/2013 | Mikhailov et al. ............. 378/19 |

* cited by examiner

METHOD FOR DETERMINING SPATIAL DISTRIBUTION AND CONCENTRATION OF A COMPONENT IN A PORE VOLUME OF A POROUS MATERIAL

CROSS-REFERENCE TO RELATED APPLICATION

This application claims priority to Russian Patent Application Serial No. RU 2011125733 filed Jun. 23, 2011, which is incorporated herein by reference in its entirety.

FIELD OF THE DISCLOSURE

This disclosure is related to methods of non-destructive analysis of porous material samples. In particular, the methods may be used for analysis of residual oil distribution, for determining natural clay concentration in a core sample or, for determining concentration of clay which has penetrated a core during drilling mud injection.

BACKGROUND OF THE DISCLOSURE

Spatial distribution of components (e.g., clay, residual fluid, absorbed films on surfaces of pores, or other solid pore volume filler) contained in pore volumes of a porous material is important information for different technical applications in medicine, petrophysics, civil engineering, material studies, and development of oil and gas fields.

There is a problem of formation damage caused by a drilling mud (or a flush liquid). This problem exists especially in long horizontal wells since many of horizontal wells are completed without casing, i.e., without a cemented and perforated flow string.

Drilling muds are complex mixtures of clay, fine particles (sized from several millimeters to less than one micron), and organic additives (polymers, surfactants, etc.) contained in a "carrying" liquid. The carrying liquid is a drilling mud "base" such as water, oil, or some synthetic liquid.

During a drilling process, a drilling mud filtrate with fines and clay contained therein penetrate a formation near a wellbore area. The formation near the wellbore area is under an excessive pressure and this causes a significant reduction of the permeability of the formation (to characterize this phenomenon the term "damage of the formation near-wellbore area" or just "formation damage" is used).

During a clean-up process (by means of gradual production starting) these components (e.g., fines and clay) are partially washed out of the near-wellbore area and its permeability partially recovers. However, a part of the components remains in pore space of the formation (absorbed on a pore surface, captured by pore throats etc.), which results in significant difference between recovered and initial permeabilities (normally, the recovered permeability does not exceed 50-70% of the initial).

A common laboratory method for checking drilling mud quality is to direct and reverse filtration through a core sample during which dynamics of permeability reduction/recovery are measured as a function of a number of injected pore volumes of the drilling mud or oil (the latter—in case of reverse pumping simulating the cleanup process).

However, clay and other drilling mud components distribution and concentration retained in the pore space along a core sample is important information for understanding mechanisms of formation damage and selection of a relevant method for improving a productivity index (minimization of a bottomhole formation zone damage). These parameters are not measured in a conventional procedure for determining drilling mud quality.

One of the most well known methods for non-destructive sample analysis is X-ray computer tomography. Thus, U.S. Pat. No. 4,540,882 describes a method for determining a drilling mud invasion using a core X-ray computer tomography with a contrast agent addition. The first material is added to the drilling mud in order to obtain a first fluid having an effective atomic number different from an effective atomic number of connate fluids contained in a formation borehole zone. A preserved core sample is collected from the borehole for scanning by a computer axial tomographic X-ray scanner to determine attenuation coefficients at a plurality of points in a cross section of the core sample. The core sample is scanned using X-rays at first and second energies. The determined attenuation coefficients for the plurality of points located in the cross section at each energy are used to determine an atomic number image for the cross section of the core sample. The depth of invasion of the first fluid is then determined from the atomic number image, as an indicator of the depth of invasion of the drilling fluid into the core sample.

Another method is disclosed in U.S. Pat. No. 4,722,095. It is based on a high X-ray attenuation coefficient of barite widely used as a weighting agent in drilling mud. First, a mud filtrate is removed from a core sample after which pore and total volume of the core sample as well as the volume of barite particles that penetrated the sample are measured using X-ray computer tomography.

Unfortunately, the use of barite as a contrasting agent to evaluate the drilling mud penetration depth is not always justified because the size of these particles is comparable with the size of pore throats and, consequently, most of them will be captured in small pores near the sample inlet.

Other drilling mud components (clay, polymers, water etc.) have weak X-ray contrast and cannot have the spatial definition with the required accuracy.

The use of contrasting agent soluble in a "carrying fluid," as it was described in U.S. Pat. No. 5,027,379, does not enable to evaluate penetration depth as well as concentration of clay and other mildly-contrasting additives contained in the drilling mud because the penetration depth of the drilling mud filtrate and the said additives is different.

SUMMARY OF THE DISCLOSURE

The disclosed method provides for improved X-ray contrast of mildly-contrasting components contained in a pore volume during computer X-ray tomography of a sample of porous material. The said components may be both natural (e.g., natural clay, film oil etc.), and embedded during filtration experiments (for example, drilling mud components).

A water-soluble salt of a metal with a high atomic weight is selected as an X-ray contrast substance providing a selective ion-exchange reaction with a component. The salt has a general formula $R^+M^-$, where $R^+$ is selected from a group consisting of $Ba^{2+}$; $Sr^{2+}$; $Tl^+$; $Rb^+$ . . . , and $M^-$ is selected from a group consisting of $Cl_n$; $NO_n$; $OHn$; $CH3COO$, $SO_4$; . . . in accordance with a standard table of water solubility for inorganic substances. The X-ray contrast substance is injected into a sample of a porous material.

Upon completion of a selective ion exchange reaction, a non-contrast displacing agent is injected into the sample. The sample is scanned by computer X-ray microtomography and spatial distribution and concentration of the component in question is estimated by analysis of the obtained computer tomographic image of the sample.

DETAILED DESCRIPTION

If an X-ray contrast substance is a water-soluble salt of a metal with a high atomic weight capable of selective ion-exchange reaction with a component in question, the heavy metal ions are accumulated on a mildly-contrasting component thus enhancing its contrast to X-ray emission. The injection of a non-contrast displacing agent upon completion of the selective ion exchange reaction results in the washout of the heavy metal salt residue and reaction products from the sample. Based on the analysis of the obtained computer tomography image (see, for example, Gonzalez, R. C. and Woods, R. E., "Digital Image Processing," Addison-Wessley, New York (1992)) spatial distribution and concentration of the component in question are determined.

In one exemplary implementation, the method is used to improve contrast to X-ray emission and subsequent determination of the concentration of clay retained in a pore volume after a direct-reverse filtration cycle of a model drilling mud (2% bentonite clay water solution) through a core sample.

A filtration experiment is performed on the injection of bentonite clay 2% water solution and subsequent washout of penetrated clay from a porous medium (reverse injection). Upon completion of the experiment, only clay strongly retained in pore throats remains in the sample pore volume.

A water-soluble salt of a metal with a high atomic weight, which enters a selective ion-exchange reaction with a clay in question, is selected as a contrast substance. Based on the bentonite clay composition ($Al_2[Si_4O_{10}](OH)_2 \cdot nH_2O$) and according to the standard table of inorganic substances solubility in water (e.g., Reference Book of Experimental Data on the Solubility of Multi-Component Water-Soluble Systems, State Science and Engineering Publishing House of Chemical Literature, Leningrad, Vol. 1-2, 1954), $BaCl_2$ is selected as the water-soluble salt of the metal.

Figure 1:
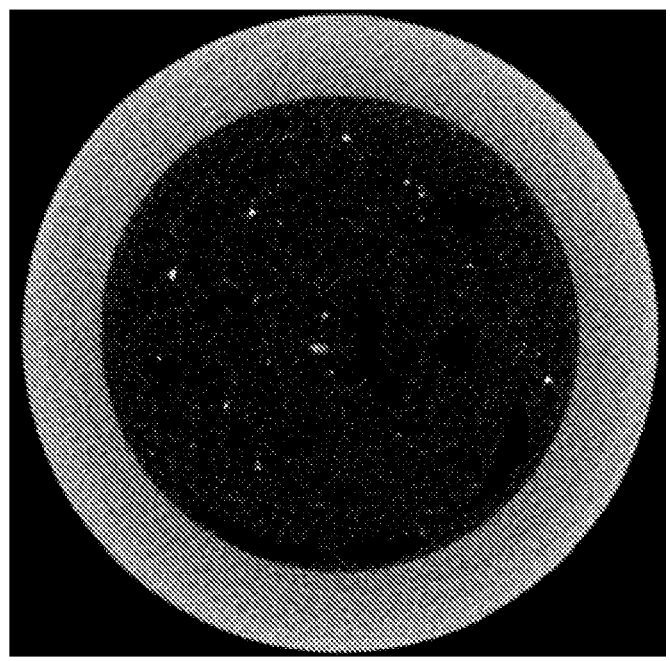
FIG. 1 shows data generated by a computer X-ray microtomography of a water solution of initial clay (before mixing with a contrast substance) and for a water solution of contrasting clay.
Figure 1:
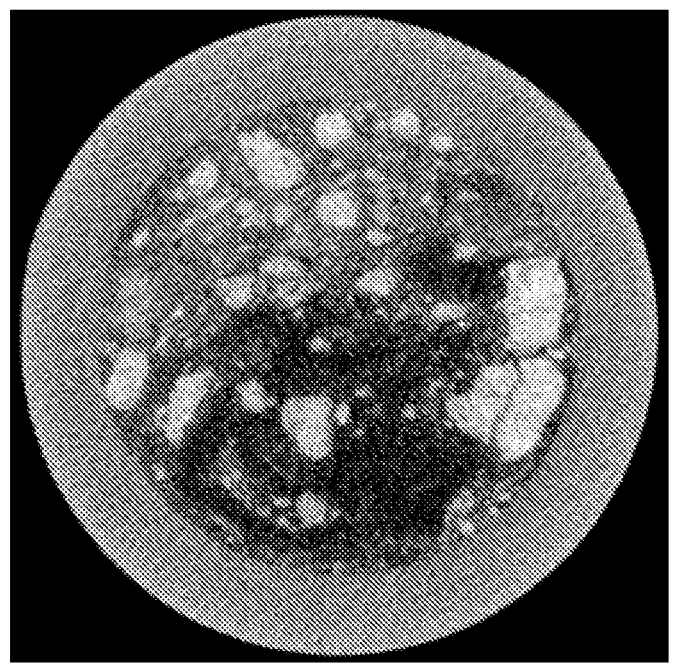

FIG. 1 shows computer X-ray microtomography data for a water solution of initial clay (before mixing with the contrast substance) and for a water solution of contrasting clay (e.g., clay subjected to the selective ion-exchange reaction with $BaCl_2$ salt).

The sample is saturated with water solution of the contrast substance ($BaCl_2$) and held for some time depending on the ion-exchange reaction rate.

Upon the completion of the ion-exchange reaction, 3-4 pore volumes of a model non-contrast displacing agent (salt solution) are pumped through the sample to remove the reaction products and contrast substance residues. An injection rate of the displacing agent must not exceed a rate of the reverse pumping in the filtration experiment.

Figure 2:
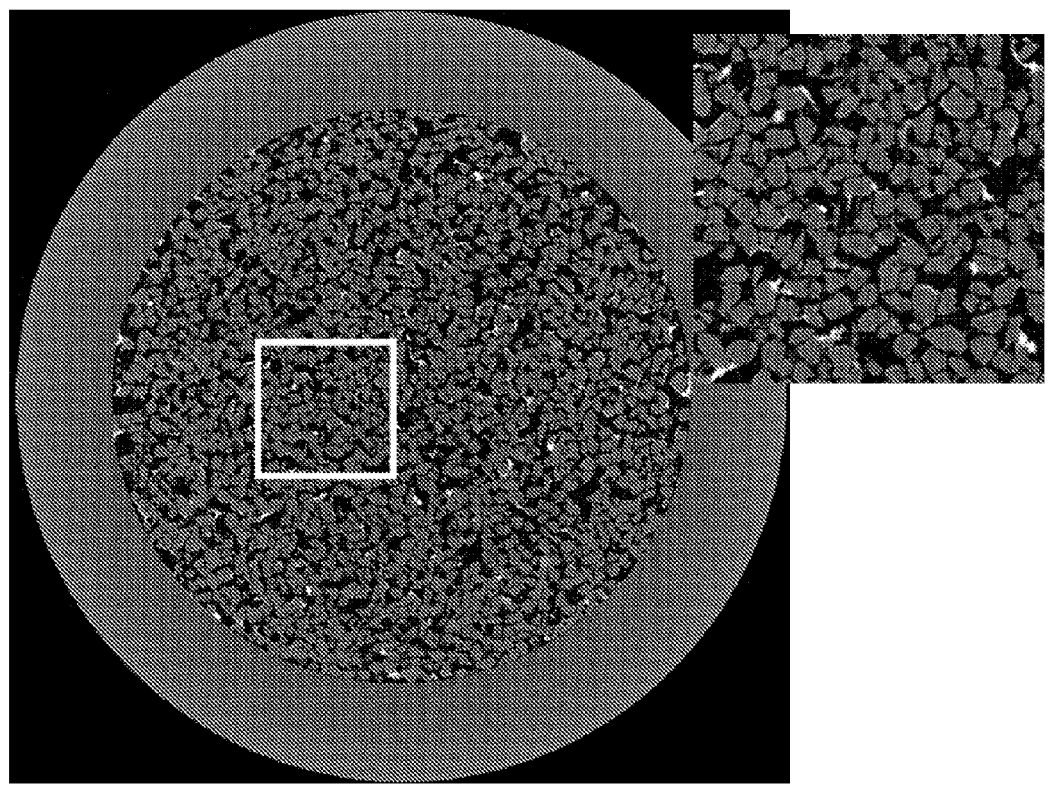
FIG. 2 shows data generated by a computer X-ray microtomography after injection of a contrast substance.

The sample is scanned by computer X-ray microtomography. An example of the sample computer X-ray microtomography after use of the contrast substance is shown in FIG. 2. Accumulation of the barium ions in the clay resulting from the ion-exchange reaction leads to significant improvement of contrast thereof (the modified clay corresponds to the white spots on the snapshot).

In another exemplary implementation, the method is used to study hydrocarbon concentration in a sample. When the sample is heated, alkanes interact with the bromine solution in an organic solvent entering into substitution reaction. It may be demonstrated by the interaction of n-dodecane $CH_3(CH_2)_{10}CH_3$ with bromine dissolved in carbon tetrachloride $CCl_4$.

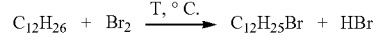

$$C_{12}H_{26} + Br_2 \xrightarrow{T, \,°C} C_{12}H_{25}Br + HBr$$

This reaction may be used for selective modification of hydrocarbons in a porous medium. The sample containing hydrocarbons is saturated with bromine solution, then heated and kept at the preset temperature. The reaction temperature and time depend on the hydrocarbon mixture composition. Upon completion of the reaction 3-4 pore volumes of a model non contrast displacing agent (salt solution) must be pumped through the sample to remove the reaction products. Bromine introduction enables enhancing contrast of the hydrocarbons in the sample pores during computer X-ray microtomography.

What is claimed is:

1. A method for determining spatial distribution and concentration of a component in a pore volume of a porous material comprising:
   selecting a water-soluble salt of a metal with a high atomic weight as an X-ray contrast substance providing a selective ion-exchange reaction with the component, the salt having a general formula $R^+M^-$, where $R^+$ is selected from a group consisting of $Ba^{2+}$; $Sr^{2+}$; $Tl^+$; $Rb^+$ . . . , $M^-$ is selected from a group consisting of $Cl_n$; $NO_n$; $OHn$; $CH3COO$, $SO_4$; . . . in accordance with a standard table of inorganic substances' water solubility,
   injecting the X-ray contrast substance into a sample of a porous material,
   upon completion of the selective ion exchange reaction injecting a non-contrast displacing agent into the sample,
   scanning the sample by computer X-ray microtomography,
   obtaining a computer tomography image of the sample and determining spatial distribution and concentration of the component by analyzing the obtained computer tomography image.

2. The method of claim 1 wherein a salt water solution is used as the non-contrast displacing agent.

* * * * *